(12) United States Patent
Flewitt et al.

(10) Patent No.: US 9,465,012 B2
(45) Date of Patent: Oct. 11, 2016

(54) MEASUREMENT METHOD USING A SENSOR; SENSOR SYSTEM AND SENSOR

(71) Applicants: Cambridge Enterprise Limited, Cambridge (GB); University of Bolton, Bolton (GB)

(72) Inventors: Andrew Flewitt, Cambridge (GB); William Milne, Newmarket (GB); Luis Garcia-Gancedo, Cambridge (GB); Jack Luo, Cambridge (GB)

(73) Assignee: Cambridge Enterprise Limited & University of Bolton (GB)

( * ) Notice: Subject to any disclaimer, the term of this patent is extended or adjusted under 35 U.S.C. 154(b) by 272 days.

(21) Appl. No.: 14/364,980

(22) PCT Filed: Dec. 14, 2012

(86) PCT No.: PCT/GB2012/053139
§ 371 (c)(1),
(2) Date: Jun. 12, 2014

(87) PCT Pub. No.: WO2013/088163
PCT Pub. Date: Jun. 20, 2013

(65) Prior Publication Data
US 2014/0331778 A1    Nov. 13, 2014

(30) Foreign Application Priority Data

Dec. 15, 2011   (GB) .................................. 1121660.3

(51) Int. Cl.
*G01N 29/00*    (2006.01)
*G01N 29/32*    (2006.01)
(Continued)

(52) U.S. Cl.
CPC .......... *G01N 29/326* (2013.01); *G01N 29/022* (2013.01); *G01N 29/036* (2013.01); *G01N 29/2437* (2013.01); *G01N 2291/0426* (2013.01)

(58) Field of Classification Search
CPC .... G01N 29/02; G01N 29/036; G01N 29/32; G01N 29/24; G03H 9/172; H03H 9/2643; H03H 9/02259; H03H 9/585; H03H 9/587; H03H 9/02228; H03H 9/02834; H03H 9/02574; H03H 3/02; H03H 3/04; H03H 3/0076; H03H 3/007; H03H 3/0077
See application file for complete search history.

(56) References Cited

U.S. PATENT DOCUMENTS 5,772,322 A    6/1998  Burns
6,293,136 B1   9/2001  Kim
(Continued)

FOREIGN PATENT DOCUMENTS

EP    0950282 B1    6/2001
GB    2474107       4/2011
(Continued)

OTHER PUBLICATIONS

Wingqvist (2010) Surface & Coatings Technology 205:1279-1286, "AlN-based sputter-deposited shear mode thin film bulk acoustic resonator (FBAR) for biosensor applications—A review".

(Continued)

*Primary Examiner* — Helen Kwok
(74) *Attorney, Agent, or Firm* — Swanson & Bratschun, L.L.C.

(57) ABSTRACT

Provided is a method for measurement of a change in environment at a sensor. The sensor has: a first layer formed of a piezoelectric material; a second layer formed adjacent the first layer and acoustically coupled with the first layer; and electrodes disposed to apply a driving signal to the first layer to generate bulk acoustic waves. The temperature coefficient of frequency of the first layer is different to that of the second layer. In the method, a first layer resonant frequency associated with the first layer and a combination resonant frequency associated with a combination of the first and second layers are detected. A shift in one or both of the first layer resonant frequency and the combination resonant frequency is detected. A portion of the shift caused by a temperature change at the sensor is identified. Another portion of the shift caused by an environmental change at the sensor other than the temperature change is identified. Also provided is a corresponding sensor and sensor system operable to carry out the method.

15 Claims, 7 Drawing Sheets

(51) Int. Cl.
  *G01N 29/02* (2006.01)
  *G01N 29/036* (2006.01)
  *G01N 29/24* (2006.01)

(56) References Cited

U.S. PATENT DOCUMENTS

| | | | | |
|---|---|---|---|---|
| 8,362,675 | B2* | 1/2013 | Chen | H03H 9/02228 310/313 R |
| 8,689,426 | B2* | 4/2014 | Thalmayr | H03H 9/02275 29/25.35 |
| 9,121,771 | B2* | 9/2015 | Tadigadapa | |
| 2002/0038989 | A1* | 4/2002 | Larson, III | H03H 3/04 310/330 |
| 2002/0190814 | A1* | 12/2002 | Yamada | B06B 1/0644 333/187 |
| 2004/0150296 | A1 | 8/2004 | Park | |
| 2004/0246075 | A1* | 12/2004 | Bradley | H03H 3/04 333/187 |
| 2005/0110598 | A1* | 5/2005 | Larson | H03H 9/02102 333/191 |
| 2005/0248238 | A1* | 11/2005 | Yamada | H03H 3/02 310/366 |
| 2006/0001329 | A1* | 1/2006 | Rao | H03H 9/02102 310/315 |
| 2006/0044078 | A1* | 3/2006 | Ayazi | H03H 3/0077 333/186 |
| 2007/0063622 | A1* | 3/2007 | Rudy | H03H 3/04 310/341 |
| 2008/0297281 | A1* | 12/2008 | Ayazi | H03H 3/0076 333/192 |
| 2009/0072663 | A1* | 3/2009 | Ayazi | H03B 5/326 310/320 |
| 2009/0289526 | A1* | 11/2009 | Sinha | H03H 9/15 310/325 |
| 2010/0045144 | A1 | 2/2010 | Koike | |
| 2010/0060111 | A1* | 3/2010 | Ayazi | H03B 5/326 310/367 |
| 2010/0194499 | A1* | 8/2010 | Wang | H03H 9/172 333/187 |
| 2010/0277034 | A1* | 11/2010 | Sinha | H03H 3/04 310/312 |
| 2011/0080233 | A1* | 4/2011 | Petit | H03H 9/02102 333/187 |
| 2011/0227671 | A1* | 9/2011 | Zhang | H04R 17/00 333/195 |
| 2011/0266917 | A1* | 11/2011 | Metzger | H03H 3/02 310/313 A |
| 2012/0262241 | A1* | 10/2012 | Phan Le | H03H 9/02259 331/154 |

FOREIGN PATENT DOCUMENTS

| | | |
|---|---|---|
| WO | WO 02/10701 | 2/2002 |
| WO | WO 2013/088163 | 6/2013 |

OTHER PUBLICATIONS

Lee, et al. (2010) Thin Solid Films 518:3000-3003, "Steady-state photoconductivity of amorphous In—Ga—Zn—O".
Rey-Mermet, et al. (2006) Sensors and Actuators B 114:681-686, "Bulk acoustic wave resonator operating at 8 GHz for gravimetric sensing of organic films".
Sauerbrey (1959) Physik 155:206-222, "Verwendung von Schwingquarzen zur Wagung dunner Schichten und zur Mikrowagung".
Razafimandimby, et al. (2006) Analog Integr Circ Sig Process 49:237-247, "A novel architecture of a tunable bandpass BAW-filter for a WCDMA transceiver".
Rai, et al., (2009) IEEE Freq. Contr. Symp. Proc. pp. 385, "A 1.5GHz CMOS/FBAR Frequency Reference with ±10ppm Temperature Stability".
Rai, et al. (2010) IEEE Transaction on Ultrasonics, Ferroelectronics, and Frequency Control 57(3):552, "A Digitally Compensated 1.5GHz CMOS/FBAR Frequency Reference".
Tada, et al. (2000) Journal of Applied Physics 87(9):4189, "Thermal expansion coefficient of polycrystalline silicon and silicon dioxide thin films at high temperatures".
Morkoc, et al. (2009) Wiley-Vch, "Zinc oxide: fundamentals, materials and device technologies".
Hirao, et al. (1991) Journal Japan. Ceram.Soc. 99:600-607, "Elastic anomaly and Structure of F-Doped Silica Glass".
Hirao, et al. (1995) Journal of Materials Science Letters 14:697-699, "Anomalous temperature dependence of the sound velocities of $SiO_2$—$TiO_2$ glasses".
Kobiakov (1980) Solid State Communications 35:305-310, "Elastic, Piezoelectric and Dielectric Properties of ZnO and CdS Single Crystals in a Wide Range of Temperatures".
Coakley, et al. (1980) IEEE Transactions on Microwave Theory and Techniques 51(3):862, "Estimation of Q-Factors and Resonant Frequencies".
Pang, et al. (2008) IEEE Electron Device Letters 9(4):315-318, "A temperature-stable film bulk acoustic wave oscillator".
Garcia-Gancedo, et al. (2010) IEEE International Ultrasonics Symposium Proceedings pp. 1064-1067, "Ultrafast sputtered ZnO thin films with high $K_T$ for acoustic wave device applications".
Garcia-Gancedo, et al. (2011) International Journal of Nanomanufacturing 7(¾):371-382, "Deposition and characterization of ultralow-stress ZnO thin films for application in FBAR-based gravimetric biosensors".
Nakamura, et al. (1981) Electronics Letters 17(14):507-509, "ZnO/$SiO_2$—diaphragm composite resonator on a silicon wafer".
Yoon, et al. (2005) IEEE International Symposium on Electronics Materials and Packaging, pp. 169-173, "Hardness and Elastic Modulus of ZnO Deposited materials by PLD Method".
Petersen, et al. (1978) IEEE Transactions on electron devices 25(10):1241-1250, "Dynamic micromechanics on Silicon".
Bjurstrom, et al. (2007) Journal of Micromechanics and Microengineering 17:651-658, "Temperature compensation of liquid FBAR sensors".
Lakin, et al. (2001) IEEE International Frequency Control Symposium and PDA Exhibition, pp. 605-608, "Temperature coefficient and ageing of BAW composite materials".
Wingqvist, et. al. (2008) Sensors and Actuators 148:88-95, "Mass sensitivity of multilayer thin film resonant BAW sensors".
GB Search Report on GB 1121660.3 dated Apr. 11, 2012.
International Search Report on PCT/GB2012/053139 dated Mar. 12, 2013.
International Preliminary Report on Patentability on PCT/GB2012/053139 dated Jun. 17, 2014.

* cited by examiner

MEASUREMENT METHOD USING A SENSOR; SENSOR SYSTEM AND SENSOR

RELATED APPLICATIONS

This application is a 35 U.S.C. §371 national phase application of PCT/GB2012/053139 (WO 2013/088163), filed on Dec. 14, 2012, entitled "Identification of Environmental Sensor Changes and Temperature Sensor Changes with a Two Layer Bulk Acoustic Wave Resonator", which application claims the benefit of Great Britain Application Serial No. 1121660.3, filed Dec. 15, 2011, which is incorporated herein by reference in its entirety.

BACKGROUND TO THE INVENTION

1. Field of the Invention

The present invention relates to a measurement method using a sensor. The sensor is typically a bulk acoustic wave resonator (BAWR), either a thin film bulk acoustic resonator (FBAR) or a solidly mounted resonator (SMR) device. The invention also relates to a sensor system incorporating such a sensor and to the sensor itself. The present invention has particular applicability, but not exclusive applicability, to the use of such a sensor in gravimetric-based sensing.

2. Related Art

EP-A-950282 [Reference 14] discloses a micromechanical resonant sensor in the form of a microbeam for use in various applications such as pressure sensing, strain sensing or as an accelerometer. The problem addressed in EP-A-950282 is that the resonant frequency of a sensor formed of a single material shifts with temperature, due to temperature-induced changes in density, elastic moduli and dimensions. EP-A-950282 addresses this problem by incorporating a material with a different coefficient of thermal expansion in order that the resultant composite microbeam has a near-zero resonant frequency shift with variations in temperature.

Pang et al (2008) [Reference 15] discloses a film bulk acoustic wave resonator (FBAR) formed using aluminium nitride and a temperature compensation material ($SiO_2$). The first order temperature coefficient of stiffness of AlN and Mo (the electrode material) is negative, whereas $SiO_2$ has a positive temperature coefficient of elastic modulus at around room temperature. By introducing a $SiO_2$ film of an appropriate thickness, the temperature dependence of the resonant frequency of the resonator can be reduced.

Garcia-Gancedo et al (2010) [Reference 16] discloses the formation of high quality ZnO films whose resonant quality is tested by generating bulk acoustic waves (BAW) in the film. FBARs were manufactured by depositing ZnO films on polished Si single crystal substrates.

It is known that FBARs and SMRs are of interest, for example, in the manufacture of gravimetric biosensors. The selective attachment or adsorption of species at the surface of the sensor reduces the resonant frequency of the device. FBARs and SMRs are of particular interest for this application due to the potential for these devices to have high quality factor (Q), to allow relatively small shifts in resonant frequency to be detected, and as such are considered to be potentially more sensitive than quartz crystal microbalances (QCM).

For example, Garcia-Gancedo et al (2011) [Reference 17] reports details of the use of a ZnO-based FBAR device as a gravimetric biosensor. Garcia-Gancedo et al (2011) points out that typical QCM devices have resonant frequencies in the range 5-20 MHz, whereas the ZnO-based FBAR devices can be formed with resonant frequencies in the range of 1.5 GHz. This significant rise in resonant frequency provides the key to increased sensitivity.

Nakamura et al (1981) [Reference 18] discloses a piezoelectric resonator of a $ZnO/SiO_2$-diaphragm supported on a silicon wafer. Nakamura et al (1981) describe a "temperature coefficient of frequency" in ppm/° C., i.e. the variation in the resonant frequency with temperature. The aim of Nakamura et al (1981) is to provide a structure which has as low a temperature coefficient of frequency as practicable. Since ZnO and $SiO_2$ respectively have positive and negative temperature coefficients of frequency, the disclosure in that document is to select a suitable thickness for the ZnO and $SiO_2$ films in order to try to provide a zero temperature coefficient of frequency for the composite structure. For the fundamental mode, it is found that the ideal ratio of the thickness of the ZnO and $SiO_2$ films is 2. The ZnO and $SiO_2$ films are formed on the silicon wafer with upper and lower electrodes sandwiching the ZnO film. The silicon wafer is etched to form the ZnO and $SiO_2$ films into a composite diaphragm structure. The actual device reported in Nakamura et al (1981) has a temperature coefficient of frequency of 10 ppm/° C. at 25° C.

SUMMARY OF THE INVENTION

Sensors of particular interest in the present invention are sensors that are sensitive to changes in stress in one or more elements of the sensor. The changes in stress may be brought about in various ways, e.g. mass loading, pressure, etc. In general terms, the change can be said to be brought about by a change in the environment of the sensor, e.g. due to the introduction of species which are able to load onto the sensor, or due to a change in the pressure of the environment.

The present inventors have realised that resonators of the type discussed above may be manufactured to be exceptionally sensitive to stress changes which they are designed to detect, but also may be sensitive even to very small changes in temperature. Therefore, even when complex efforts have been made in order to try to provide temperature compensation, it is in practice impossible to provide perfect temperature compensation across a broad temperature range. The present inventors therefore propose a different approach. The present invention has been devised in order to address at least one of the above problems. Preferably, the present invention reduces, ameliorates, avoids or overcomes at least one of the above problems.

In general terms, the new approach is to design a sensor based on a resonator device so that detectable resonances behave differently in response to temperature changes than in response to stress changes. In this way, changes in the resonant frequency can be attributed to the correct cause. This constitutes a general aspect of the invention.

Accordingly, in a first preferred aspect, the present invention provides a method for measurement of a change in environment at a sensor, the method including the step of providing a sensor having:
 a first layer formed of a piezoelectric material;
 a second layer formed adjacent the first layer and acoustically coupled with the first layer; and
 electrodes disposed to apply a driving signal to the first layer to generate bulk acoustic waves,
wherein the temperature coefficient of frequency of the first layer is different to that of the second layer,
the method further including the steps:

detecting a first layer resonant frequency associated with the first layer and a combination resonant frequency associated with a combination of the first and second layers;

detecting a shift in one or both of the first layer resonant frequency and the combination resonant frequency;

identifying a portion of the shift caused by a temperature change at the sensor; and identifying another portion of the shift caused by an environmental change at the sensor other than the temperature change.

The term "temperature coefficient of frequency" is used here as in Nakamura et al (1981). The acoustic velocity of bulk acoustic waves in a material typically changes with temperature. Furthermore, thermally-induced dimensional changes affect the resonant frequency of a body of material subjected to the bulk acoustic waves. Thus, the temperature coefficient of frequency of a material can be considered to describe the behaviour of the resonant frequency of the material subjected to bulk acoustic waves with temperature.

In a second preferred aspect, the present invention provides a sensor suitable for measuring a change in environment at the sensor, the sensor having:

a first layer formed of a piezoelectric material;

a second layer formed adjacent the first layer and acoustically coupled with the first layer, the second layer being formed of a different material to the first layer, the temperature coefficient of frequency of the first layer being different to that of the second layer; and electrodes disposed to apply a driving signal to the first layer to generate bulk acoustic waves, the sensor being operable to allow:

detection of a first layer resonant frequency associated with the first layer and a combination resonant frequency associated with a combination of the first and second layers;

detection of a shift in one or both of the first layer resonant frequency and the combination resonant frequency;

identification of a portion of the shift caused by a temperature change at the sensor; and identification of another portion of the shift caused by an environmental change at the sensor other than the temperature change.

In a third preferred aspect, the present invention provides a sensor system suitable for measuring a change in environment at a sensor, the sensor system including a sensor and an analysis device, the sensor having:

a first layer formed of a piezoelectric material;

a second layer formed adjacent the first layer and acoustically coupled with the first layer, the second layer being formed of a different material to the first layer, the temperature coefficient of frequency of the first layer being different to that of the second layer; and electrodes disposed to apply a driving signal to the first layer to generate bulk acoustic waves, the analysis device being operable to:

detect a first layer resonant frequency associated with the first layer and a combination resonant frequency associated with a combination of the first and second layers;

detect a shift in one or both of the first layer resonant frequency and the combination resonant frequency;

identify a portion of the shift caused by a temperature change at the sensor; and identify another portion of the shift caused by an environmental change at the sensor other than the temperature change.

The first and/or second aspect of the invention may have any one or, to the extent that they are compatible, any combination of the following optional features.

Preferably, the temperature coefficients of frequency of the first layer and second layer are such that a change in temperature results in the first layer resonant frequency and the combination resonant frequency each shifting in opposite directions. Thus, a change in temperature may increase the first layer resonant frequency and decrease the combination resonant frequency, or a change in temperature may decrease the first layer resonant frequency and increase the combination resonant frequency. The effect of this to an observer is that a temperature change motivates the first layer resonant frequency and the combination resonant frequency either to shift towards each other or to shift apart.

Preferably, an environmental change at the detector other than a temperature change results in the first layer resonant frequency and the combination resonant frequency each shifting in the same direction. Thus, the environmental change (other than a temperature change) may decrease the first layer resonant frequency and decrease the combination resonant frequency. In some circumstances, it is possible for the environmental change to increase the first layer resonant frequency and increase the combination resonant frequency. However, in other circumstances, the first layer resonant frequency and the combination resonant frequency decrease in response to the environmental change.

The environmental change of interest is preferably one which affects a level of stress on or in the first and/or second layer. Typically, increasing the stress on or in the first and/or second layer results in the first layer resonant frequency and the combination resonant frequency to decrease. The environmental change of interest is preferably one or more of: change in environmental pressure to which the sensor is subjected; change in liquid pressure to which the sensor is subjected; mechanical deformation of the sensor; illumination of the sensor; mass loading on a surface of the sensor. Mass loading may be achieved in response to specific binding of a species of interest at the surface, by suitable treatment of the surface. Such an approach is of particular interest to bio-sensing. In that case, the environmental change is the introduction of the species of interest to the sensor. Mass loading may also be achieved in response to specific chemical reactions of a gas of interest at the surface, by suitable treatment of the surface. Such an approach is of particular interest to gas-sensing. In that case, the environmental change is the introduction of the gas of interest to the sensor. Mass loading may also be achieved in response to specific chemical reactions at the surface due to humidity, by suitable treatment of the surface. Such an approach is of particular interest to humidity-sensing. In that case, the environmental change is the variation of environmental humidity to which the sensor is subjected.

Suitable applications for the sensor include all applications for which FBARs and SMRs are already known, e.g. as a frequency filter, pressure sensor, temperature sensor, humidity sensor, mass sensor, gas sensor, bio-sensor, light sensor. The benefit over existing FBAR and SMR sensors is that it is not necessary with the preferred embodiments of the invention to provide a constant-temperature environment, reference sensors or temperature readout circuits.

In addition, the sensor is of particular utility for applications requiring simultaneous detection of a combination of any two (or more) of the following physical variables: pressure, temperature, mass, gas, humidity.

Furthermore, the sensor is particularly useful for applications that benefit from decreasing the overall size (taking into account packaging and/or electronics) of the existing sensors capable of measuring two physical variables.

Some examples of suitable applications are:

Simultaneous detection of gas concentration/temperature: automobile/aerospace cabin air quality assessment, engine gas emissions, households/commercial buildings gas detection.

Simultaneous detection of temperature and mass load: bio-sensing, thickness monitoring in thin film deposition systems, water monitoring systems (detection of contaminated water in developing countries for example).

Simultaneous detection of temperature and environmental pressure (or humidity): weather monitoring systems, vacuum chambers conditions monitoring systems.

Simultaneous detection of temperature and mechanical deformation: touch sensors.

It will be clear from the explanation above that the environmental change in combination with the temperature change can result in a relatively complex shifting of the resonant frequencies of interest. The net effect may be to shift one of the resonant frequencies more than the other. By assessing the magnitude and direction of the net shift of both resonant frequencies, it is possible to identify the portion of the shift attributable to change in temperature and the portion of the shift attributable to the environmental change other than the change in temperature.

The first layer resonant frequency is preferably a fundamental mode resonance set up in the first layer alone. Alternatively, the first layer resonant frequency may be a low order (e.g. first or second) resonance set up in the first layer alone. The resonance represents a standing wave of the bulk acoustic waves reflected between opposing surfaces of the first layer.

The combination resonant frequency is preferably a fundamental mode resonance set up in the first and second layers. Alternatively, the combination resonant frequency may be a low order (e.g. first or second) resonance set up in the first and second layers. The resonance represents a standing wave of the bulk acoustic waves reflected between opposing surfaces of the first layer and the second layer but not from the interface between the first and second layers. There may of course be arrangements provided in which a wave is confined in the individual layers separately.

Preferably the temperature coefficient of frequency in the first and second layers is dominated by the variation with temperature of the velocity of propagation of longitudinal acoustic waves in the first and second layers. Note that it is also contemplated that the invention can work suitably on the basis of thickness shear modes in the layers. Preferably, the velocity of propagation of longitudinal acoustic waves in the first layer decreases with temperature. For example, a variation of about $-12$ ppm·K$^{-1}$ (at room temperature) is found to be suitable. Preferably, the velocity of propagation of longitudinal acoustic waves in the second layer increases with temperature. For example, a variation of about 70 ppm·K$^{-1}$ (at room temperature) is found to be suitable. The effect of this is that the first layer resonant frequency decreases with a temperature rise and the combination resonant frequency increases with a temperature rise.

One of the electrodes is typically an interposed electrode, provided between the first and second layers. However, preferably the combination resonance is not provided by reflections from a surface of the interposed electrode.

Preferably, the thickness of the first and second layer is similar (e.g. of the same order of magnitude). This allows differentiation between the first layer resonant frequency and the combined resonant frequency. The thickness of the first and second layer may, for example, differ by only a factor of two or less, more preferably less than two. Still more preferably, the thickness of the first and second layer are substantially the same. This allows the most suitable differentiation of the first layer resonant frequency and the combined resonant frequency.

The thickness of the first layer is preferably 10 µm or less. More preferably, the thickness of the first layer is 5 µm or less. Similarly, the thickness of the second layer is preferably 10 µm or less. More preferably, the thickness of the second layer is 5 µm or less. Thickness values of about 2 µm for each of the first and second layer are found to be suitable, for example.

Preferably, each resonant frequency of interest is in the frequency range above 100 MHz, more preferably in the frequency range of 400 MHz or higher. Still more preferably, each resonant frequency of interest is in the frequency range 600 MHz or higher.

Preferably, the quality factor of each resonance of interest is at least 500. More preferably, the quality factor is at least 1000. The quality factor is measured by the 3 dB method.

Preferably, the sensor is a gravimetric-based sensor. Using the invention, a mass sensitivity of about $10^{-15}$ g can be achieved.

The first layer may be formed of any suitable piezoelectric material. For example, the first layer may be formed of one or more of: ZnO, AlN, PZT, lithium niobate.

The first and second layers may be single crystal and/or epitaxial layers. However, this is not essential. Preferably, the piezoelectric properties of the first layer are similar to the piezoelectric properties of the bulk material.

The second layer may be formed of a different material to the first layer. The material of the second layer may be any suitable material that has a temperature coefficient of frequency of opposite sense to that of the piezoelectric layer. The second layer may be piezoelectric or non-piezoelectric, the choice of material for the second layer therefore being wider than the choice for the first layer. Non-piezoelectric materials are preferred for simplicity. For example, the second layer may be formed of one or more of: $SiO_2$, silicon nitride, aluminium oxide, hafnium oxide, titanium oxide.

The first and second layers are preferably formed on a substrate. The substrate may be any suitable material that provides mechanical support for the first and second layers. For example, a single crystal substrate may be used. Silicon is a suitable material for the substrate.

Preferably, the sensor has an active area. At the active area, it is preferred that the first and second layers are not supported by the substrate. This allows the first and second layers freedom to resonate. The active area may be provided in the form of a diaphragm, coinciding with a hole in the substrate. In this way, the substrate can provide support to the first and second layers around the hole. The hole may be formed by etching of the substrate. Suitable etching processes are known which allow the manufacture of the sensor to be tightly controlled, by control of the dimensions of the hole and thus of the diaphragm.

The present inventors have also realised that the present invention need not be limited to the situation where only two layers are provided. For example, a third layer may be formed adjacent the second layer and acoustically coupled with the second layer. This then allows the generation of one or more further combination resonant frequencies, for example associated with a combination of the first, second and third layers, or associated with a combination of the second and third layers. Preferably, the temperature coefficient of frequency of the third layer is different to that of the first and/or second layer. Preferably, the material of the third layer is different to the material of the first and second layers. In this way, it possible for the shift behaviour of the resonant frequencies to be attributed to three or more different physical variables, in a similar manner to the attribution of the shift behaviour to two physical variables as described above.

Further optional features of the invention are set out below.

BRIEF DESCRIPTION OF THE DRAWINGS

Embodiments of the invention will now be described by way of example with reference to the accompanying drawings in which:

FIG. 3(a): mode I (754 MHz); FIG. 3(b): first harmonic of mode I (2.26 GHz); FIG. 3(c) mode II (1.44 GHz); FIG. 3(d): first harmonic of mode II (4.34 GHz).

Figure 1:
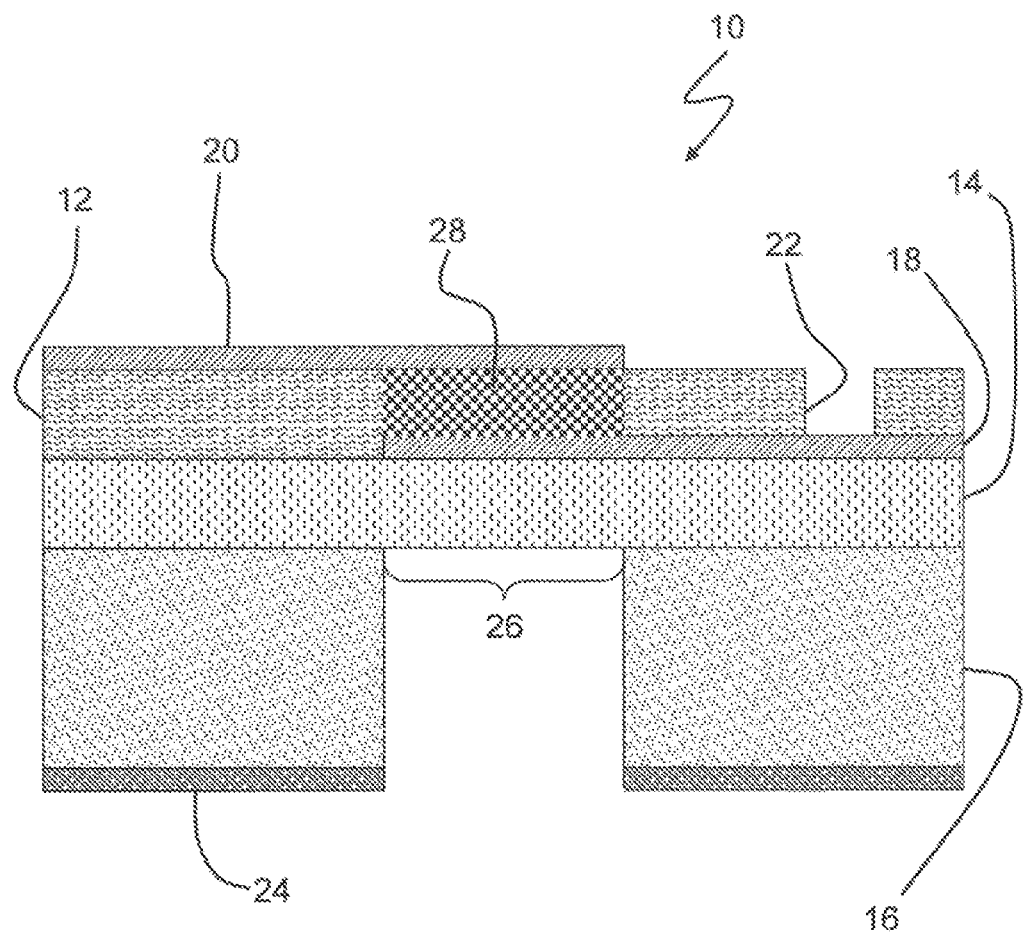
FIG. 1 shows a schematic cross sectional view of a device according to an embodiment of the invention. Note that the aspect ratio of the device (i.e. the x and y axes of the drawings) is not to scale.

DETAILED DESCRIPTION OF THE PREFERRED EMBODIMENTS, AND FURTHER OPTIONAL FEATURES OF THE INVENTION

Over the last decade there has been an increased interest in developing highly sensitive resonators for gravimetric biosensing [References 1-3]. Thin film technology has been adopted as the optimum approach for the fabrication of high frequency (GHz range) bulk acoustic wave (BAW) resonators. The frequency of resonance $f_r$ is dependent on the device structure and size and the acoustical properties of the films utilised for their fabrication. The application of an external force on the resonator's surface induces additional stresses on the thin films which in turn lowers $f_r$. The magnitude of the frequency shift is a function of the external force applied. By tracking changes in $f_r$, mass changes on the resonators (for example due to the adsorption of biological samples) can be detected. The total mass bound on the resonator's surface is proportional to the change in $f_r$.

The magnitude of the frequency shift, $\Delta f_r$, for a given mass load is proportional to the square of $f_r$ [Reference 4]. Therefore, resonators working at higher frequencies are capable, in theory, of achieving a better sensitivity. This is because a greater $\Delta f_r$ is induced for the same change in mass. However, higher $f_r$ and smaller device dimensions cause all environmental and boundary conditions to affect the operation of the BAW resonators more strongly than for resonators with lower $f_r$.

One of the most important challenges to be overcome is the resonant frequency drift with temperature, which can result in undesirable false-positive/negative responses.

The speed of propagation of acoustic waves within a material is generally dependent on the temperature. Also, the thickness of a thin film typically changes with changes in temperature (up to several ppm·$K^{-1}$) depending on the coefficients of thermal expansion (CTE) of the material. Therefore, resonant frequency shifts of up to several kHz can occur due to a change in temperature. This can be considered as a temperature coefficient of frequency. These resonant frequency shifts are indistinguishable from those due to mass loading. Therefore for some known devices, sensing must be carried out in an environment where the temperature is constant. This is clearly impractical for various reasons.

To overcome this issue, a reference device isolated from the species to be measured can be used in addition to the sensing device [Reference 5]. With this arrangement, $\Delta f_r$ due to a mass load can be extrapolated from the $\Delta f_r$ measured on the sensing device and the $\Delta f_r$ measured on the reference device. Alternatively, temperature readout circuitry can be integrated with the resonator and real-time temperature compensation can be implemented via software processing [Reference 6 and 7]. Either of these techniques, however, increases the cost of the sensor, the physical size of the sensor and requires relatively complex electronics.

The preferred embodiment of the present invention uses a thin film bulk acoustic wave resonator (FBAR) or a solidly mounted resonator (SMR) specifically designed to support two different fundamental resonant modes at different frequencies with opposite reactions to temperature and mass changes. This device allows direct discrimination of frequency shifts due to mass or temperature changes thereby eliminating the need for a reference device and complex electronics.

We have manufactured devices supporting simultaneously two fundamental modes of resonance by depositing a piezoelectric thin film on a non-piezoelectric film, the thickness of each film being of similar magnitude. One fundamental mode corresponds to the resonance of the bi-layer stack (the combination resonance—called "mode I" in parts of this detailed description) and occurs when a half wavelength equals the combined thickness of the piezoelectric and non-piezoelectric layers. The other fundamental mode corresponds to the resonance of the piezoelectric layer alone and occurs when a half wavelength equals the thickness of this layer (the first layer resonance—called "mode II" in parts of this detailed description). When the thickness of the piezoelectric and non-piezoelectric layers are not of similar magnitude, then both modes would occur at frequencies close to each other and would couple into a single mode. The frequency of resonance of mode I is influenced by the velocity of acoustic wave propagation within both layers, as in Equation 1, and the frequency of resonance of mode II is influenced by the velocity of propagation within the piezoelectric layer only. It must be noted that when a half wavelength equals the thickness of the non-piezoelectric film (second layer) there is produced no resonance.

$$V_t = \frac{t_1 v_1 + t_2 v_2}{t_1 + t_2} \quad \text{(Equation 1)}$$

where $V_t$ is the velocity of propagation affecting mode I, $t_1$ and $t_2$ are respectively the thickness of the first and second layers, and $v_1$ and $v_2$ are respectively the velocities of propagation within the first and second layers.

As well as the velocity of acoustic wave propagation, the frequency of resonance of both modes changes depending on the coefficients of thermal expansion of both materials. This is because the thickness of the layers changes with temperature due to the CTE.

By appropriate selection of the piezoelectric and non-piezoelectric film materials (and properties), a dual-mode sensor device with modes having opposite reactions to temperature can be realized.

One device manufactured in this work is illustrated in FIG. 1. The device 10 consists of a first layer, being a thin film 12 of ZnO (2 μm) reactively sputtered on a second layer, being a thin film 14 of $SiO_2$ (2 μm), which was thermally grown on a Si (111) substrate 16. A bottom electrode 18 (formed of Cr/Au) was defined by photolithography and was deposited on the $SiO_2$ before sputtering the ZnO. A top electrode 20 was also defined by photolithography and aligned to the bottom electrodes. A via 22 through the ZnO to the bottom electrode was achieved by wet-etching the ZnO. Finally, the Si from the back of the wafer was removed through an $Al_2O_3$ hard mask 24 with a DRIE process to release a $SiO_2$/ZnO membrane 26 of area 200×200 μm.

On application of a suitable driving signal between electrodes 18 and 20, bulk acoustic waves are generated in active region 28, corresponding to the part of the ZnO film sandwiched between overlapping electrodes 18 and 20.

Figure 2:
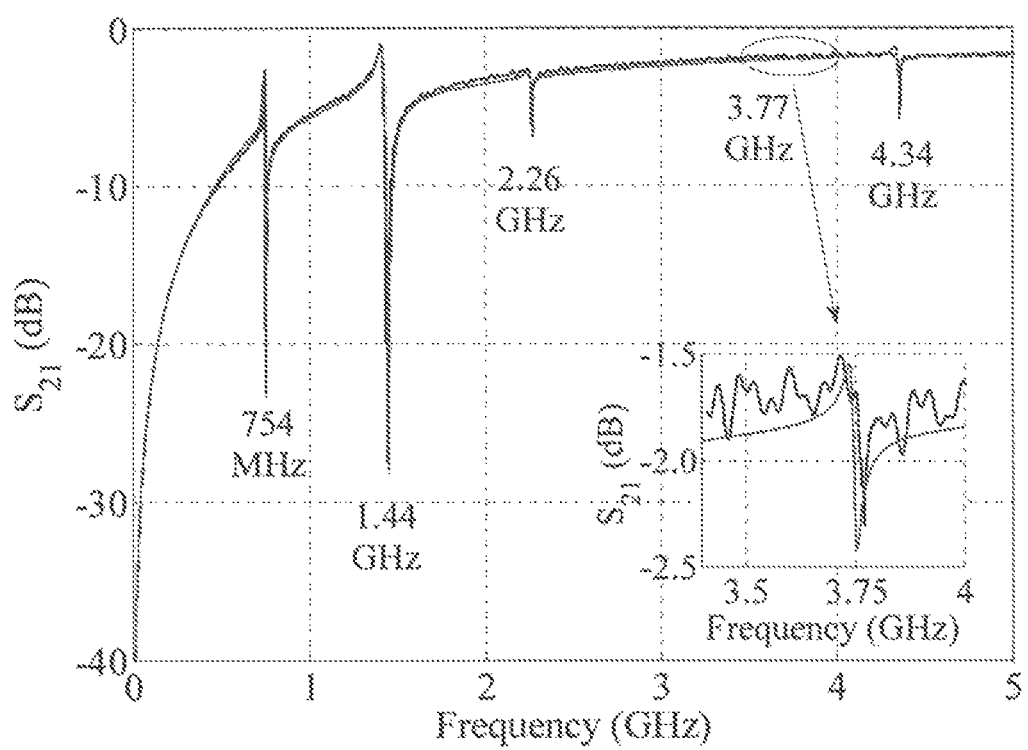
FIG. 2 shows the typical frequency response ($S_{21}$) of a device according to FIG. 1. The smooth line is the simulated frequency response and the other line is the experimental frequency response. The first fundamental mode is at 754 MHz, and the second is at 1.44 GHz. The first and second harmonics of the first mode are found at 2.26 GHz and 3.77 GHz (×3 and ×5 times the fundamental frequency). The first harmonic of mode 2 is at 4.34 GHz.

The resonant frequencies of the FBAR devices were measured with a coplanar probe station on a GSG configuration connected to a network analyser, and are shown in FIG. 2. Two fundamental modes of resonance are observed at 754 MHz (mode I) and 1.44 GHz (mode II), with their first harmonics at 2.26 GHz and 4.34 GHz respectively. The second harmonic of mode I is found at 3.77 GHz (inset of FIG. 2).

Mode I is the combination resonance (fundamental mode) and corresponds to the resonance of the $SiO_2$/ZnO bi-layer stack and occurs when a half wavelength equals the combined thickness of the ZnO and $SiO_2$ layers. Mode II is the first layer resonance (fundamental mode) and corresponds to the resonance of the ZnO layer alone and occurs when a half wavelength equals the thickness of the ZnO layer, but it is also greatly influenced by the mass-load introduced by the $SiO_2$ layer. Therefore a variation in the thickness of either layer will affect both resonance modes and their harmonics. The quality factor Q of both fundamental modes was calculated using the 3 dB method [Reference 13] and found to be 2200 and 1400 for modes I and II respectively.

Figure 3:
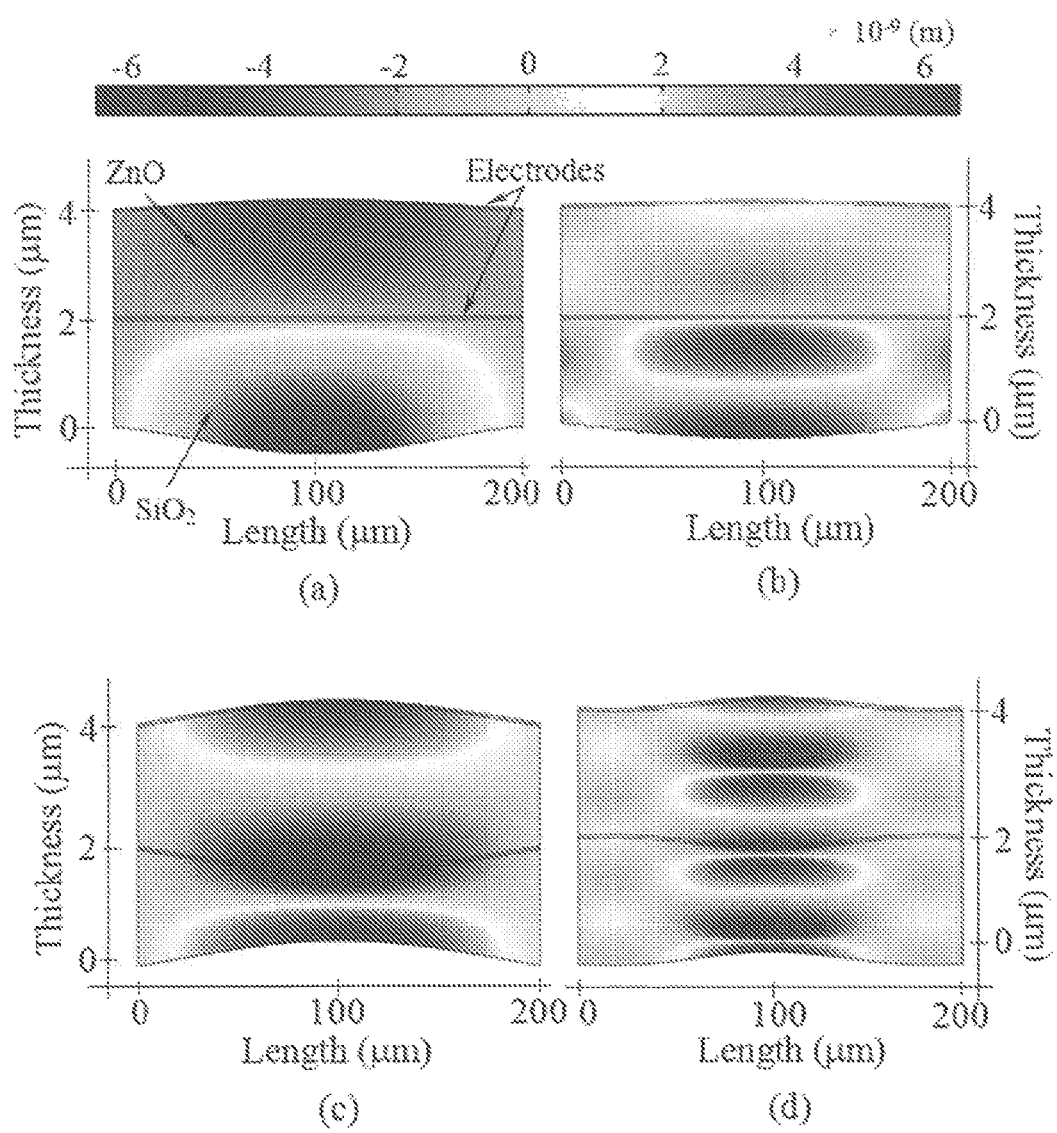
FIGS. 3(a)-(d) show simulated cross sectional views of the deformation of the device diaphragm at resonance.

Theoretical analysis of the resonance modes was carried out using FEA, and the numerical simulations were consistent with the experiments as in FIG. 2. FIG. 3 shows a cross sectional view of the simulated deformation of the devices at resonance. FIG. 3(a) shows the deformation at 754 MHz (mode I) and FIG. 3(b) shows the deformation of the first harmonic of mode I, at 2.26 GHz. FIG. 3(c) shows the deformation at 1.44 GHz (mode II) and (d) shows the deformation of the first harmonic of mode II, at 4.34 GHz. It can be seen that both modes correspond to two different types of longitudinal waves. It should be noted that the x and y axis are plotted with different scales. As seen in FIG. 3(b) there is only small deformation in the ZnO films for Mode I first harmonic but large deformation in the $SiO_2$ film. $SiO_2$ has greater deformation and may achieve greater mass sensitivity when this layer is used as the sensing layer. However, this has been difficult to achieve experimentally in the past. $SiO_2$ provides greater deformation due to its lower Elastic modulus (about 60 GPa) compared to that of ZnO (about 170 GPa). See, for example, References 19 and 20.

The original images shown in FIG. 3 used false colour. In FIG. 3(a), a minimum value (i.e. about $-6 \times 10^{-9}$ m) is found at the bottom centre of the $SiO_2$ layer. A maximum value (i.e. about $6 \times 10^{-9}$ m) is found at the top centre of the ZnO layer. In FIG. 3(b), a minimum value (i.e. about $-6 \times 10^{-9}$ m) is found at the bottom centre of the $SiO_2$ layer. A maximum value (i.e. about $6 \times 10^{-9}$ m) is found at the top centre of the $SiO_2$ layer. In FIG. 3(c), maximum values (i.e. about $6 \times 10^{-9}$ m) are found at the top centre of the ZnO layer and the bottom centre of the $SiO_2$ layer. A minimum value (i.e. about $-6 \times 10^{-9}$ m) is found between these maxima. In FIG. 3(d), maximum values (i.e. about $6 \times 10^{-9}$ m) are found at the top centre of the ZnO layer and the bottom centre of the $SiO_2$ layer. Alternating minima and maxima are found between.

Both $SiO_2$ and ZnO possess positive coefficients of thermal expansion (of 0.5 ppm·$K^{-1}$ and about 2.5 to about 5 ppm·$K^{-1}$ respectively) [References 8 and 9]. Hence a temperature rise increases the thickness of both layers, motivating a decrease of the resonant frequencies of both modes in the absence of any other effect. However, a temperature rise causes the velocity of propagation of longitudinal waves (e.g. bulk acoustic waves) to increase in $SiO_2$ (about 70 ppm·$K^{-1}$) [References 10 and 11] and to decrease in ZnO (about $-12$ ppm $K^{-1}$) [References 9 and 12]. This effect is greater than the effect of the effect of thermal expansion. The combined effect on the resonant frequency caused by a change of temperature is a temperature coefficient of frequency of about 69.5 ppm·$K^{-1}$ and $-7.5$ ppm·$K^{-1}$ for $SiO_2$ and ZnO respectively. As a consequence, a temperature rise lowers the frequency of resonance of mode II (first layer resonance) due to the lower speed of the wave propagation within the ZnO layer (unaffected by the change in the speed of propagation within the $SiO_2$ layer). Mode I (combination resonance) is affected by both the change in the velocity of propagation within the $SiO_2$ and within the ZnO layer. Therefore, by careful design of the $SiO_2$/ZnO layers thickness ratio, the frequency shift of this mode due to temperature variation can be controlled and utilised as a temperature reference for mass load sensing.

The fabricated devices described above are such that mode I exhibits a positive frequency shift with a temperature rise, while mode II shows a negative frequency shift for the same temperature variation. This was achieved with a 1:1 ZnO:$SiO_2$ thickness ratio.

In this way, by monitoring simultaneously both resonance modes, it is known whether any observed frequency shift is due to a mass load or to a temperature change. If both the modes exhibit a negative frequency shift, then a mass has been loaded on the resonators. Alternatively if the resonances exhibit frequency shifts of opposite signs then there has been a variation of temperature.

It should be noted that the variation of velocity of acoustic wave propagation within a material over a wide range of temperatures is in general non-linear. Hence it would not be possible, using the same basic principles, to design a device in which the first mode shows no frequency shift with temperature. By careful choice of the materials and thickness ratio of the piezo and non-piezo films, the linear temperature dependence of the frequency can be eliminated, but the effects of the non-linear terms will still be present. Hence the devices described here, in which more than one resonance mode is observed, provide an ideal method to discriminate the nature of any observed frequency drift.

Figure 4:
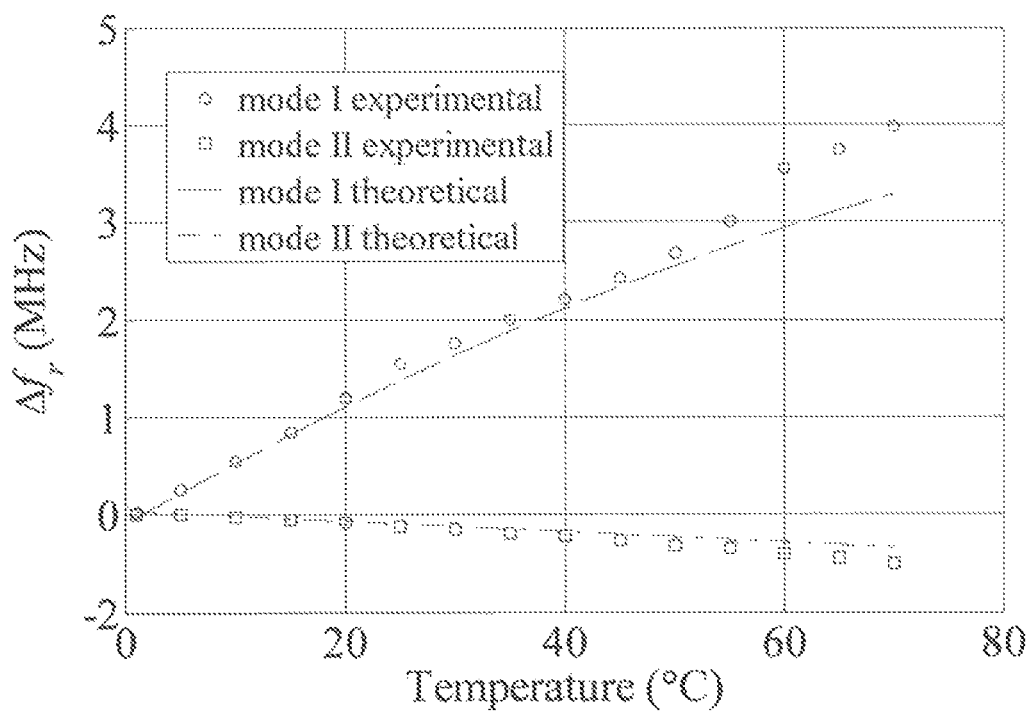
FIG. 4 shows $\Delta f_r$ for modes I and II at different temperatures.

The frequency response of the devices fabricated was studied experimentally as a function of temperature. The results are shown in FIG. 4. The temperature was controlled by placing the devices, wire bonded to 50 Ohm transmission line PCBs, into a solid brass environmental isolation assembly with a high thermal mass. This assembly was placed onto the metallic output pads of a HAAKE K20 water bath, which pumped a thermal fluid at fixed rate and controllable temperature. This allowed the control of the temperature of the FBAR within less than ±0.5° C. of the set temperature as measured by an automated thermocouple (National Instruments TC 01) with a resolution of 0.1° C. and a response time of less than 1 second.

As expected, the $f_r$ of mode II decreases with increase of temperature and the $f_r$ of mode I rises. The absolute frequency shift $|\Delta f_r|$ of mode I is about 60 ppm·K$^{-1}$, much larger than the about −5.0 ppm·K$^{-1}$ for mode II due to the higher variation in the speed of wave propagation within the SiO$_2$/ZnO stack layer compared to within the ZnO layer alone. Both the measured values are comparable to those theoretical ones predicted by FEA. The differences between the theoretical and experimental results are believed to be caused by the fact that literature CTE and sound velocity changes with temperature values have been used within the FEA model; however these values are largely dependent on the technologies used for their growth and the quality of the material obtained.

Figure 5:
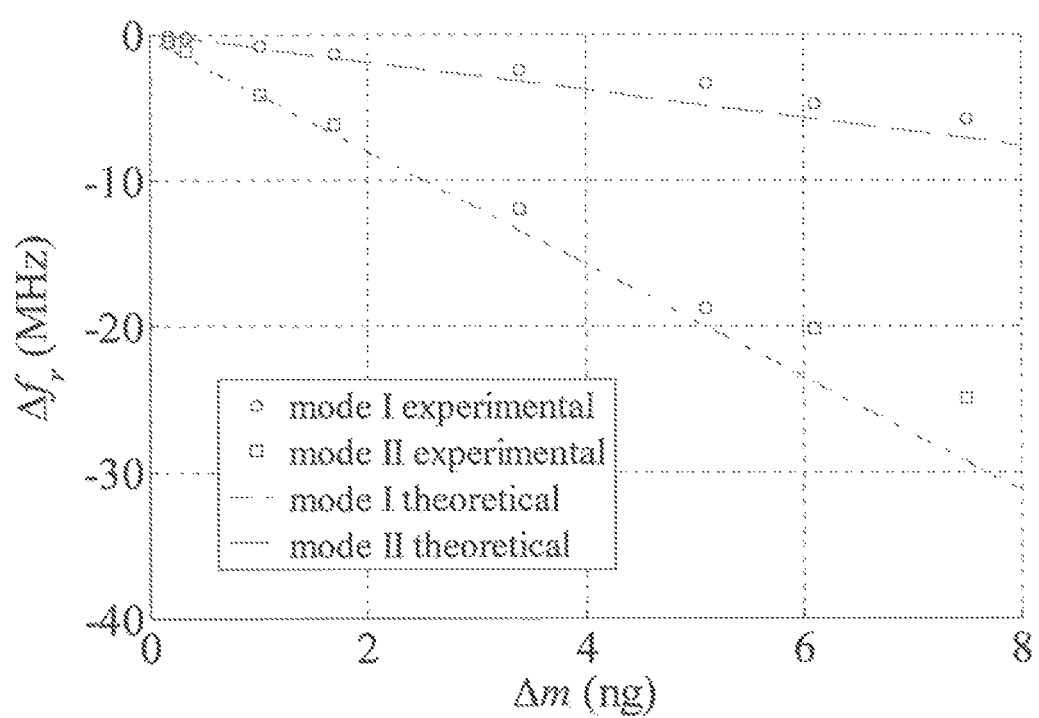
FIG. 5 shows $\Delta f_r$ (at room temperature) for modes I and II for different mass loads on the resonator's surface.

When an additional mass is added onto a resonator's surface, then the stresses induced affect both layers and a negative frequency shift is observed on both resonance modes and their harmonics. This has been verified experimentally by sputtering thin gold layers of different thickness on top of the resonators. The exact mass load which is being added can be precisely calculated from the additional layer thickness, lateral dimensions of the resonant area and the mass density of the gold. The $f_r$ of modes I and II (fundamental modes) decreases linearly due to mass loads within the mass load range studied. The $\Delta f_r$ observed for different mass loads is shown in FIG. 5 together with FEA predictions. It is noted that mode II has a larger mass load sensitivity and hence it is suggested to be used for mass sensing.

Figure 6:
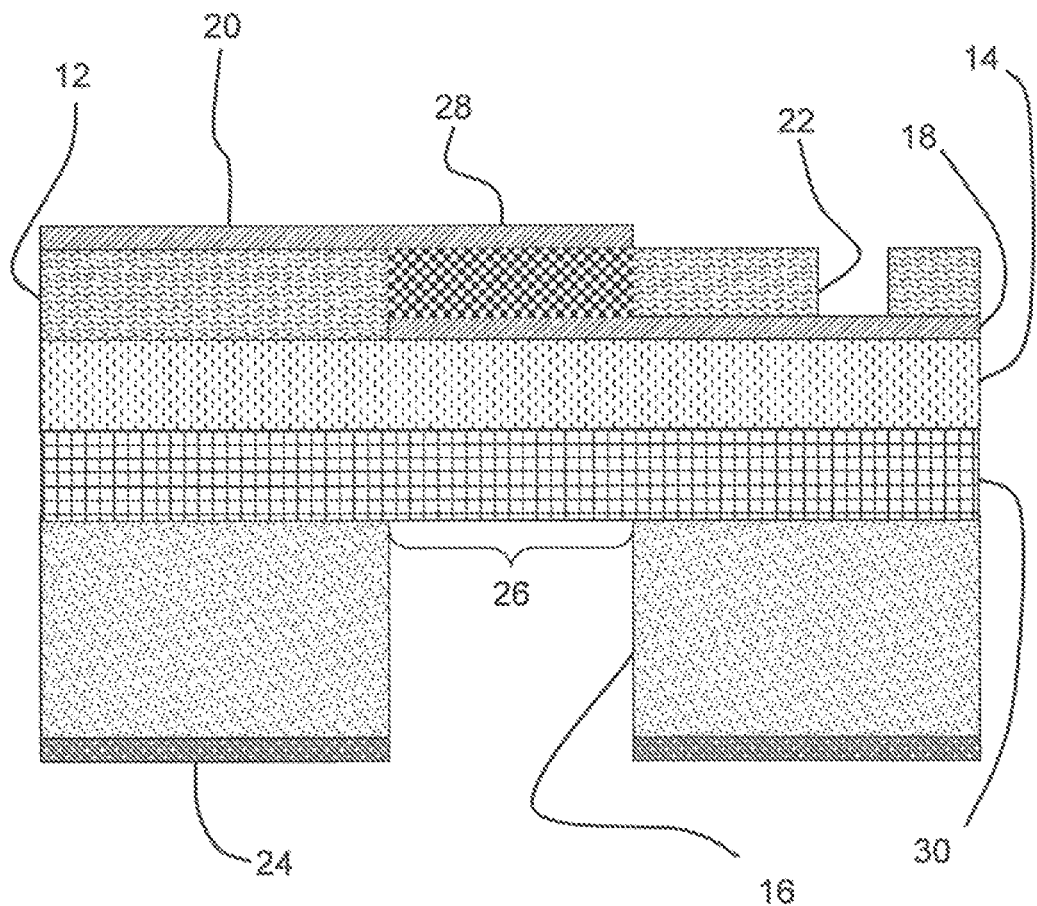
FIG. 6 shows a schematic cross sectional view of a device according to another embodiment of the invention. Note that the aspect ratio of the device (i.e. the x and y axes of the drawings) is not to scale.

FIG. 6 shows a schematic cross sectional view of a device according to another embodiment of the invention. Note that the aspect ratio of the device (i.e. the x and y axes of the drawings) is not to scale. This device is identical to the device of FIG. 1 with the exception that a third layer 30 is provided. All other features of FIG. 6 are given the same reference numerals as in FIG. 1 and those features are not described further here.

Third layer 30 is typically formed of a 2 µm layer of SiN. First layer 12 is formed of a 2 µm layer of ZnO and second layer 14 is formed of a 2 µm layer of SiO$_2$.

Figure 7:
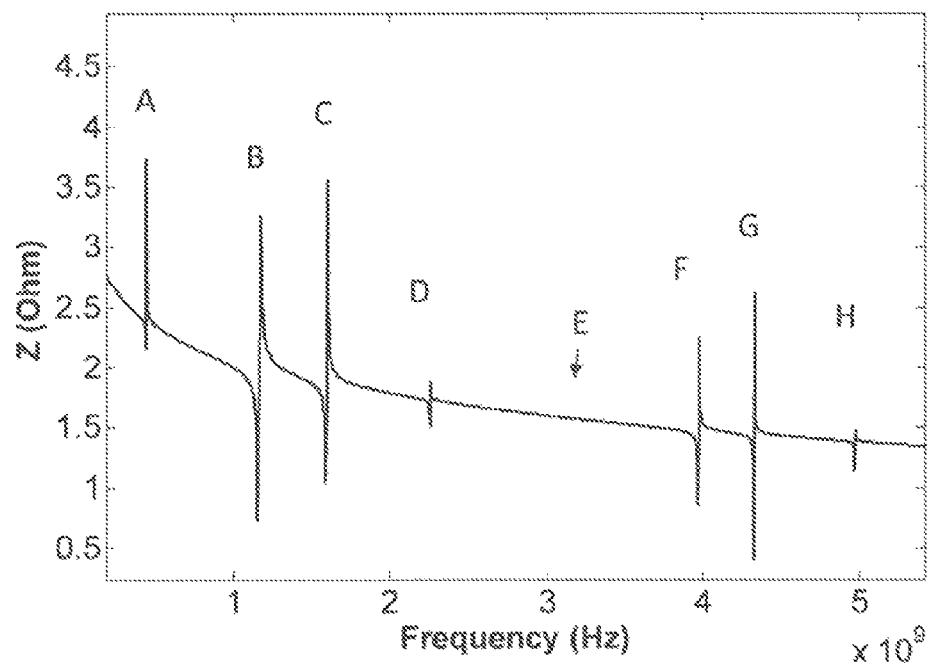
FIG. 7 shows the predicted frequency response (Z) of a resonator formed by a 2 μm layer (first layer) of ZnO, a 2 μm layer (second layer) of $SiO_2$ and a 2 μm layer (third layer) of SiN.

FIG. 7 shows the predicted frequency response (Z) of a resonator according to the structure shown in FIG. 6. The various resonances are identified as A-H as follows:

Mode A: 451 MHz (Fundamental). This corresponds to a combination resonance of all three layers. It is therefore equivalent to Mode I in the device if FIG. 1, but occurring at lower frequency due to the thicker device (6 µm for three-layers compared to 4 µm for two-layers).

Mode B: 1150 MHz (Fundamental). This corresponds to the ZnO (first layer) vibrating, similar to Mode II in the device of FIG. 1, but occurring at lower frequency due to the greater mass loading effect introduced by the additional SiN layer.

Mode C: 1550 MHz (Fundamental). This corresponds to resonance of the second and third layers (the SiO$_2$/SiN stack). It is interesting to note that an equivalent mode is not seen in the device of FIG. 1. Without wishing to be bound by theory, this is possibly due to different acoustic impedances/velocities of propagation.

Mode D: 2260 MHz (×5 Mode A)

Mode E: 3251 MHz (×7 Mode A)

Mode F: 3990 MHz (×9 Mode A)

Mode G: 4430 MHz (probable ×3 Mode C)

Mode H: 4980 MHz (×11 Mode A)

Figure 8:
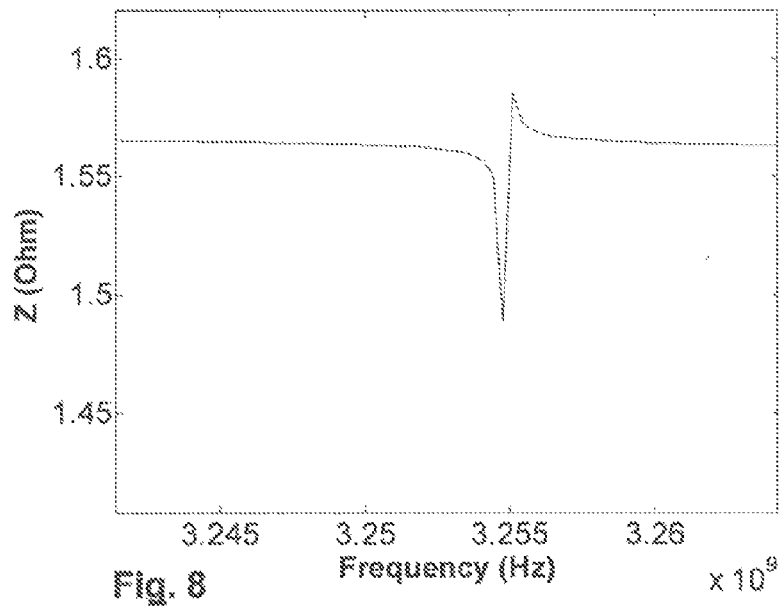
FIG. 8 shows an enlarged view of Mode E response from FIG. 7.

FIG. 8 shows an enlarged view of Mode E response from FIG. 7, between 3.24 GHz and 3.27 GHz.

Therefore the three fundamental modes are seen, along with harmonics of at least the first fundamental mode.

As shown in FIG. 6, the third layer is located below the second layer. The electrodes configuration is the same as for the device of FIG. 1. Any additional layers (4th, 5th . . . nth) can be stacked under the third layer.

The material for the third layer can, in principle, be piezoelectric. However, this is not necessary (as for the second layer). The RF signal, as for the device of FIG. 1, is applied to the first layer.

The third layer may be formed of any suitable material, e.g. SiO$_2$, SiN, AlO$_x$, HfO, TiO, ZnO, AlN, LiNbO$_3$ provided that the third layer is different to the second layer.

For devices having more than three layers, the more complex becomes the frequency response. However, in principle, the frequency response and its change in response to environmental stimulus can be analysed.

The physical variables to be measured correspond to a selection of three of those measurable with the device of FIG. 1. As an example, when the third layer is a light-sensitive materials, the sensor can discriminate light as well as mass and temperature, by looking at the frequency shifts in the third resonance, and how they relate to the other resonances. Alternatively, when the third layer expands/compresses when subjected to environmental pressure in opposite way to the first and second layers it is possible to discriminate pressure, as well as mass and temperature.

The present disclosure therefore shows the fabrication of FBARs and SMRs which support simultaneously two (or more) modes of resonance at different frequencies, corresponding to two (or more) different types of longitudinal acoustic waves or thickness shear modes. These resonance modes are harnessed in order to exhibit different reactions to mass loads and temperature variations. Hence one single device provides information on whether any observed frequency shift is due to a mass load or temperature change. This avoids undesired false responses without the need of additional reference devices or complicated electronics for real-time temperature compensation. The device is of particular interest for gravimetric sensing.

As will be understood from this disclosure, a sensor system according to the preferred embodiment of the invention incorporates a sensor as described above, in combination with an analysis device. The analysis device in the laboratory setting may be a controller such as a personal computer, but in a stand-alone system, the analysis device may include dedicated electronics. The analysis device is capable of supplying suitable frequency signals to the sensor in order to drive the different resonances required, and to detect the required resonant frequencies and to detect any shift in those resonant frequencies. The analysis device further provides an interface to provide results to a user, typically in the form of a graphical display, to identify a part of the detected frequency shift attributable to a temperature change and to identify a remaining part of the detected frequency shift attributable to an environmental change (other than a temperature change).

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

LIST OF REFERENCES

Reference 1: G. Wingqvist, Surf. & Coat. Tech. 205, 1279 (2010).
Reference 2: T-Y. Lee and J-T. Song, Thin Solid Films 518, 6630 (2010).
Reference 3: S. Rey-Mermet, R. Lanz et al., Sens. & Act. B 114, 681 (2005).
Reference 4: G. Sauerbrey, Z. Physik 155, 206 (1959)
Reference 5: S. Razafimandimby, C. Tilhac et al., Anal. Integ. Circ. & Sign. Proc. 49, 237 (2006)
Reference 6: S. Rai, Y. Su et al., IEEE Freq. Contr. Symp. Proc. p. 385 (2009)
Reference 7: S. Rai, Y. Su et al., IEEE Trans. Ultr. Ferr. Freq. Contr. 57, 552 (2010)
Reference 8: H. Tada, A. E. Kumpel et al., J. App. Phys. 87, 4189 (2000)
Reference 9: H. Morkoc and U. Ozgur, in: "Zinc oxide: fundamentals, materials and device technologies", Wiley-Vch (2009)
Reference 10: K. Hirao, T. Kawano et al., J. Japan. Ceram. Soc. 99, 600 (1991)
Reference 11: K. Hirao, K. Tanaka et al., J. Mat. Sci Lett. 14, 697 (1995)
Reference 12: I. B. Kobiakov, Sol. Stat. Commun. 35, 305 (1980)
Reference 13: K. J. Coakley, J. D. Splett et al., IEEE Trans. Micro. Theo. & Tech. 51, 862 (2003)
Reference 14: EP-A-950282
Reference 15: Pang et al (2008) [W. Pang, R. Ruby, R. Parker, P. Fisher, M. Unkrich and J. Larson, "A temperature-stable film bulk acoustic wave oscillator" IEEE Electron Device Letters Vol. 29, No. 4, 2008, 315-318]
Reference 16: Garcia-Gancedo et al (2010) [L. Garcia-Gancedo, J. Pedros, A. Flewitt, W. Milne, G. Ashley, J. Luo and C. Ford "Ultrafast sputtered ZnO thin films with high $k_T$ for acoustic wave device applications" 2010 IEEE International Ultrasonics Symposium Proceedings, 1064-1067]
Reference 17: Garcia-Gancedo et al (2011) [L. García-Gancedo, G. M. Ashley, X. B. Zhao, J. Pedrós, A. J. Flewitt, W. I. Milne, J. K. Luo, J. R. Lu, C. J. B. Ford, D. Zhang "Deposition and characterisation of ultralow-stress ZnO thin films for application in FBAR-based gravimetric biosensors" International Journal of Nanomanufacturing 2011—Vol. 7, No. 3/4 pp. 371-382]
Reference 18: Nakamura et al (1981) [K. Nakamura, H, Sasaki and H. Shimizu "ZnO/SiO$_2$-diaphragm composite resonator on a silicon wafer" Electronics Letters, Vol. 17 No. 14 (1981) pp. 507-509]
Reference 19: H. Yoon and Y. YU "Hardness and Elastic Modulus of ZnO Deposited materials by PLD Method", IEEE International Symposium on Electronics Materials and Packaging, pp. 169-173, 2005
Reference 20: K. E. Petersen, "Dynamic micromechanics on Silicon", IEEE Transactions on electron devices, Vol. 25, No. 10, p. 1241-1250, 1978

The invention claimed is:

1. A method for measurement of a change in environment at a sensor, the method including the step of providing the sensor having:
   a first layer formed of a piezoelectric material;
   a second layer formed adjacent the first layer and acoustically coupled with the first layer; and
   electrodes disposed to apply a driving signal to the first layer to generate bulk acoustic waves,
   wherein a temperature coefficient of frequency of the first layer is different to that of the second layer,
   the method further including the steps:
   detecting a first layer resonant frequency associated with the first layer and a combination resonant frequency associated with a combination of the first and second layers;
   detecting a shift in one or both of the first layer resonant frequency and the combination resonant frequency;
   identifying a portion of the shift caused by a temperature change at the sensor; and
   identifying another portion of the shift caused by an environmental change at the sensor other than the temperature change.

2. The method according to claim 1 wherein the temperature coefficients of frequency of the first layer and the second layer are such that a change in temperature results in the first layer resonant frequency and the combination resonant frequency each shifting in opposite directions.

3. The method according to claim 1 wherein the environmental change at the sensor other than a temperature change results in the first layer resonant frequency and the combination resonant frequency each shifting in the same direction.

4. The method according to claim 1 wherein the environmental change is one which affects a level of stress on or in the first and/or second layer.

5. The method according to claim 4 wherein the environmental change is one or more of: change in gas pressure to which the sensor is subjected; change in liquid pressure to which the sensor is subjected; mechanical deformation of the sensor; mass loading on a surface of the sensor.

6. The method according to claim 5 wherein the mass loading is achieved in response to specific binding of a species of interest at a surface of the sensor.

7. The method according to claim 1 wherein the first layer resonant frequency is a fundamental mode resonance set up in the first layer alone.

8. The method according to claim 1 wherein the combination resonant frequency is a fundamental mode resonance set up in the first and second layers.

9. The method according to claim 1 wherein a thickness of the first and second layer are substantially the same.

10. The method according to claim 1 wherein the first layer is formed of ZnO.

11. The method according to claim 1 wherein the second layer is formed of $SiO_2$.

12. The method according to claim 1 wherein the first and second layers are formed on a substrate, the sensor having an active area, the first and second layers not being supported by the substrate at the active area.

13. A sensor for measuring a change in environment at the sensor, the sensor having:
   a first layer formed of a piezoelectric material;
   a second layer formed adjacent the first layer and acoustically coupled with the first layer, the second layer being formed of a different material to the first layer, a temperature coefficient of frequency of the first layer being different to that of the second layer; and
   electrodes disposed to apply a driving signal to the first layer to generate bulk acoustic waves,
the sensor configured to allow:
   detection of a first layer resonant frequency associated with the first layer and a combination resonant frequency associated with a combination of the first and second layers;
   detection of a shift in one or both of the first layer resonant frequency and the combination resonant frequency;
   identification of a portion of the shift caused by a temperature change at the sensor; and
   identification of another portion of the shift caused by an environmental change at the sensor other than the temperature change.

14. The sensor according to claim 13 wherein the sensor is a gravimetric-based sensor having a mass sensitivity of about $10^{-15}$ g.

15. A sensor system for measuring a change in environment at a sensor, the sensor system including the sensor and an analysis device, the sensor having:
   a first layer formed of a piezoelectric material;
   a second layer formed adjacent the first layer and acoustically coupled with the first layer, the second layer being formed of a different material to the first layer, a temperature coefficient of frequency of the first layer being different to that of the second layer; and
   electrodes disposed to apply a driving signal to the first layer to generate bulk acoustic waves,
the analysis device configured to:
   detect a first layer resonant frequency associated with the first layer and a combination resonant frequency associated with a combination of the first and second layers;
   detect a shift in one or both of the first layer resonant frequency and the combination resonant frequency;
   identify a portion of the shift caused by a temperature change at the sensor; and
   identify another portion of the shift caused by an environmental change at the sensor other than the temperature change.

* * * * *

UNITED STATES PATENT AND TRADEMARK OFFICE
CERTIFICATE OF CORRECTION

PATENT NO. : 9,465,012 B2
APPLICATION NO. : 14/364980
DATED : October 11, 2016
INVENTOR(S) : Flewitt et al.

Page 1 of 1

It is certified that error appears in the above-identified patent and that said Letters Patent is hereby corrected as shown below:

(72) Inventors should read: Andrew Flewitt, Cambridge, United Kingdom
William Milne, Newmarket, United Kingdom
Luis Garcia-Gancedo, Cambridge, United Kingdom
Jack Luo, United Kingdom
Gregor Ashley-James, Bolton, United Kingdom Signed and Sealed this
Twenty-second Day of May, 2018

Andrei Iancu
*Director of the United States Patent and Trademark Office*